United States Patent [19]
Ockuly et al.

[11] Patent Number: 5,640,955
[45] Date of Patent: Jun. 24, 1997

[54] GUIDING INTRODUCERS FOR USE IN THE TREATMENT OF ACCESSORY PATHWAYS AROUND THE MITRAL VALVE USING A RETROGRADE APPROACH

[75] Inventors: John D. Ockuly, Minnetonka; James A. Hassett, Bloomington, both of Minn.

[73] Assignee: Daig Corporation, Minnetonka, Minn.

[21] Appl. No.: 388,800

[22] Filed: Feb. 14, 1995

[51] Int. Cl.$^6$ .............. A61B 5/04; A61B 17/39; A61N 1/05
[52] U.S. Cl. .............. 128/642; 606/41; 607/122
[58] Field of Search ................... 128/642, 772; 607/122, 98, 99; 606/41

[56] References Cited

U.S. PATENT DOCUMENTS

| | | | |
|---|---|---|---|
| 4,033,331 | 7/1977 | Guss et al. | |
| 4,117,836 | 10/1978 | Erikson | |
| 4,641,649 | 2/1987 | Walinsky et al. | |
| 4,882,777 | 11/1989 | Narula | |
| 4,883,058 | 11/1989 | Ruiz | |
| 4,898,591 | 2/1990 | Jang et al. | |
| 4,945,912 | 8/1990 | Langberg | |
| 5,016,640 | 5/1991 | Ruiz | |
| 5,215,540 | 6/1993 | Anderhub | |
| 5,231,994 | 8/1993 | Harmjanz | |
| 5,242,441 | 9/1993 | Avitall | |
| 5,427,119 | 6/1995 | Swartz et al. | 604/280 |
| 5,476,495 | 12/1995 | Kordis et al. | 607/122 |
| 5,564,440 | 10/1996 | Swartz et al. | 607/122 |
| 5,575,766 | 11/1996 | Swartz et al. | 604/53 |

OTHER PUBLICATIONS

Singer, I, et al., "Catheter Ablation for Arrhythmias," Clinical Manual of Electrophysiology, pp. 421–431 (1993).
Falk, R.H., et al., "Atrial Fibrillation, Mechanisms and Management", pp. 359–374 (1992).
Horowitz, L.N. "Current Management of Arrhythmias" pp. 373–378 (1991).
Gallagher, J.J. et al. "Catheter Technique for Closed Chest Ablation of the Atrioventricular Conduction System," N. Engl. J. Med., vol. 306, pp. 194–200 (1982).
Tracy, C.M., "Radiofreauency Catheter Ablation of Ectopic Atrial Tachy Cardia using Paced Activation Sequence Mapping" J. Am. Coll. Cardiol., vol. 21, pp. 910–917 (1993).
Saul, J.P. et al. "Catheter Ablation of Accessory Atrioventricular Pathways in Young Patients: Use of Long Vascular Sheaths, The Transseptal Approach and A Retrograde Left Posterior Parallel Approach" J. Amer. Coll. Card. vol. 21, No. 3, pp. 571–583 (1993).
Swartz, J.F. et al. "Radiofrequency Endocardial Catheter Ablation of Accessory Atrioventricular Pathway Atrial Insection Sites" Circulation, vol. 87, No. 2, pp. 487–499 (1993).

Primary Examiner—Lee S. Cohen
Attorney, Agent, or Firm—Scott R. Cox

[57] ABSTRACT

A process for the mapping and/or ablation of accessory pathways around the mitral valve using a retrograde approach by use of ablation and/or mapping catheters guided by precurved guiding introducers. Also disclosed are shapes for the guiding introducers to be used for the ablation and/or mapping of the accessory pathways around the mitral valve using a retrograde approach.

11 Claims, 7 Drawing Sheets

CUT AWAY VIEW OF HEART SHOWING A LATERAL RETROGRADE GUIDING INTRODUCER FOR SUPPORTING A CATHETER TO ABLATE A LEFT LATERAL ACCESSORY PATHWAY

AV GROOVE
(AS VIEWED FROM ABOVE)

L = LATERAL
A = ANTERIOR
S = SEPTAL
PS = POSTERO SEPTAL
P = POSTERIOR

CUT AWAY VIEW OF HEART SHOWING
A LATERAL RETROGRADE GUIDING
INTRODUCER FOR SUPPORTING A
CATHETER TO ABLATE A LEFT LATERAL
ACCESSORY PATHWAY

LATERAL

POSTERIOR

POSTERO SEPTAL

SEPTAL

ANTERIOR

GUIDING INTRODUCERS FOR USE IN THE TREATMENT OF ACCESSORY PATHWAYS AROUND THE MITRAL VALVE USING A RETROGRADE APPROACH

BACKGROUND OF INVENTION

1. Field of Invention

This invention relates to introducers. More particularly, this invention relates to guiding introducers of specific shapes for use within the left ventricle of the human heart for the treatment of accessory pathways around the mitral valve.

2. Prior Art

Introducers and catheters have been in use for medical procedures for many years. For example, one use has been to convey an electrical stimulus to a selected location within the human body. Another use is to monitor and make measurements for diagnostic tests within the human body. Catheters may be used by a physician to examine, diagnose and treat while positioned at a specific location within the body which is otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters. Thus, there are a number of references which disclose catheters with predetermined shapes, designed for use during specific medical procedures generally associated with the heart or the vascular system. Because of precise physiology of the heart and the vascular system, catheters or introducers with precisely designed shapes for predetermined uses within the human heart and vascular system are increasingly important.

Catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps. 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February 1993).

U.S. Pat. No. 4,641,649 discloses the use of high frequency energy for the treatment of tachycardia or cardiac dysrhythmia. See also U.S. Pat. No. 4,945,912 for the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation Vol. 87, pp. 487–499 (1993). See also Tracey, C. N. "Radio Frequency Catheter Ablation of Ectopic Atrial Tachycardia Using Paced Activation Sequence Mapping" J. Am. Coll. Cardiol. Vol. 21, pp. 910–917 (1993). See also U.S. Pat. Nos. 5,172,699, 5,222,501 and 5,242,441.

Accordingly, it is an object of this invention to prepare a guiding introducer for selected medical procedures in the left ventricle.

It is a further object of this invention to prepare a guiding introducer for use in selected electrophysiology procedures within the left ventricle of the heart.

Another object of this invention is to prepare a guiding introducer for use in selected ablation procedures within the left ventricle of the heart.

These and other objects are obtained by the design of the guiding introducers disclosed in the instant invention.

SUMMARY OF INVENTION

The instant invention includes a process for the ablation and mapping of accessory pathways around the mitral valve of the left ventricle of the heart using a retrograde approach comprising (a) introducing into the left ventricle a precurved, guiding introducer, wherein said guiding introducer contains a lumen running lengthwise therethrough, a proximal and a distal end and wherein the introducer is comprised of shaped first, second and third sections;

(b) introducing into the lumen of the guiding introducer an ablation and/or mapping catheter containing a proximal and distal end, wherein said catheter has one or more electrodes located at or near the distal end of the catheter;

(c) guiding the catheter to a selected location about the mitral valve of the heart on the ventricular side by use of the guiding introducer; and (d) mapping and/or ablating the selected location about the mitral valve by use of the electrodes of the catheter.

In addition, the instant invention is a guiding introducer to be used in the left ventricle comprised of a first, second and third sections wherein the first section is a generally elongated straight section which is merged at its distal end with the second and a third section which forms a complex curved section.

DETAILED DESCRIPTION OF THE DRAWINGS

Figure 1A:
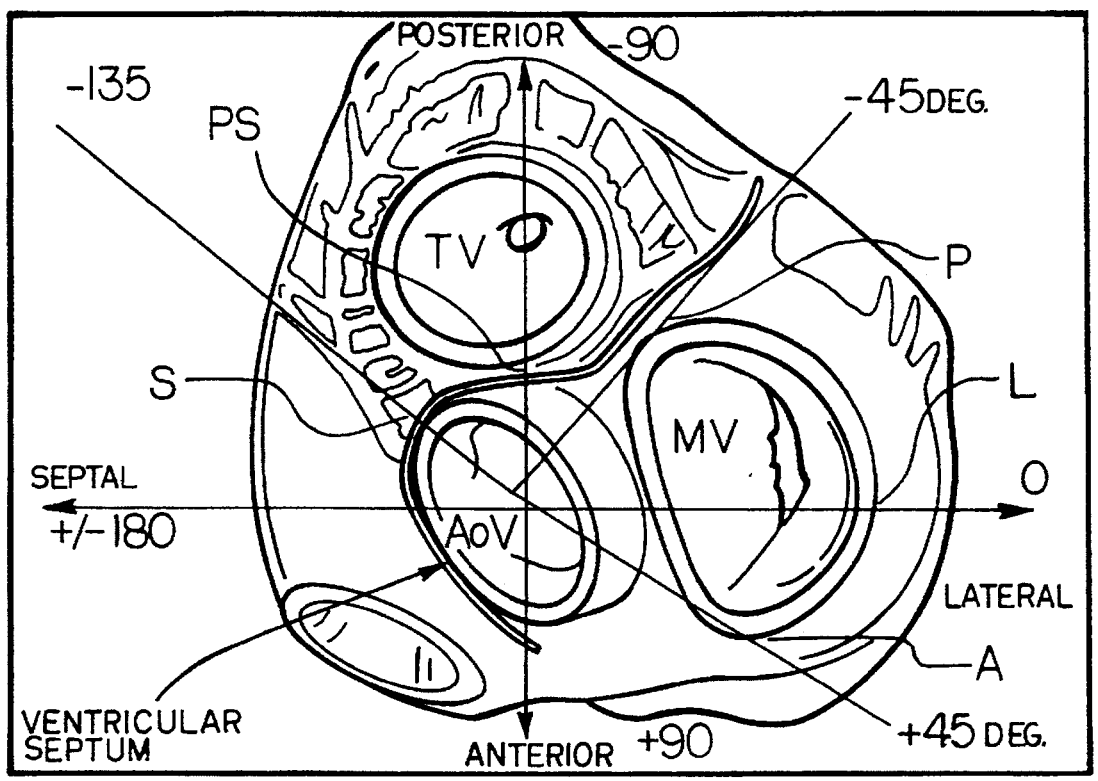
FIG. 1A is a cross-section from above the heart of a portion of the left side of the heart showing the mitral valve, aortic valve, tricuspid valve and pulmonary valve defining the position of those features of the heart relative to the aortic valve.

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. The mitral valve contained within the atrioventricular septum communicates the left atrium with the left ventricle. See FIG. 1A. On the inner wall of the right atrium, where it is connected with the left atrium, is a recessed portion, the fossa ovalis. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electrochemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome (W-P-W) have an arrhythmia. The cause of this arrhythmia is the existence of an anomalous conduction pathway or pathways that connect the atria muscle tissue directly to the ventricular muscle tissue, thus by-passing the normal His-Purkinje system. These pathways are usually located in the fibrous tissue that connect the atrium and the ventricle. In recent years a technique has been developed to destroy these anomalous conduction pathways by delivering energy into the tissue in which the pathways exist. To accomplish this procedure a special catheter with ablation electrodes is positioned as close as possible to the anomalous conduction pathway to maintain constant tissue contact while energy is delivered to destroy the pathway. This same type of contact with the cardiac tissue is also necessary when mapping or other procedures are employed relating to these pathways.

Figure 1B:
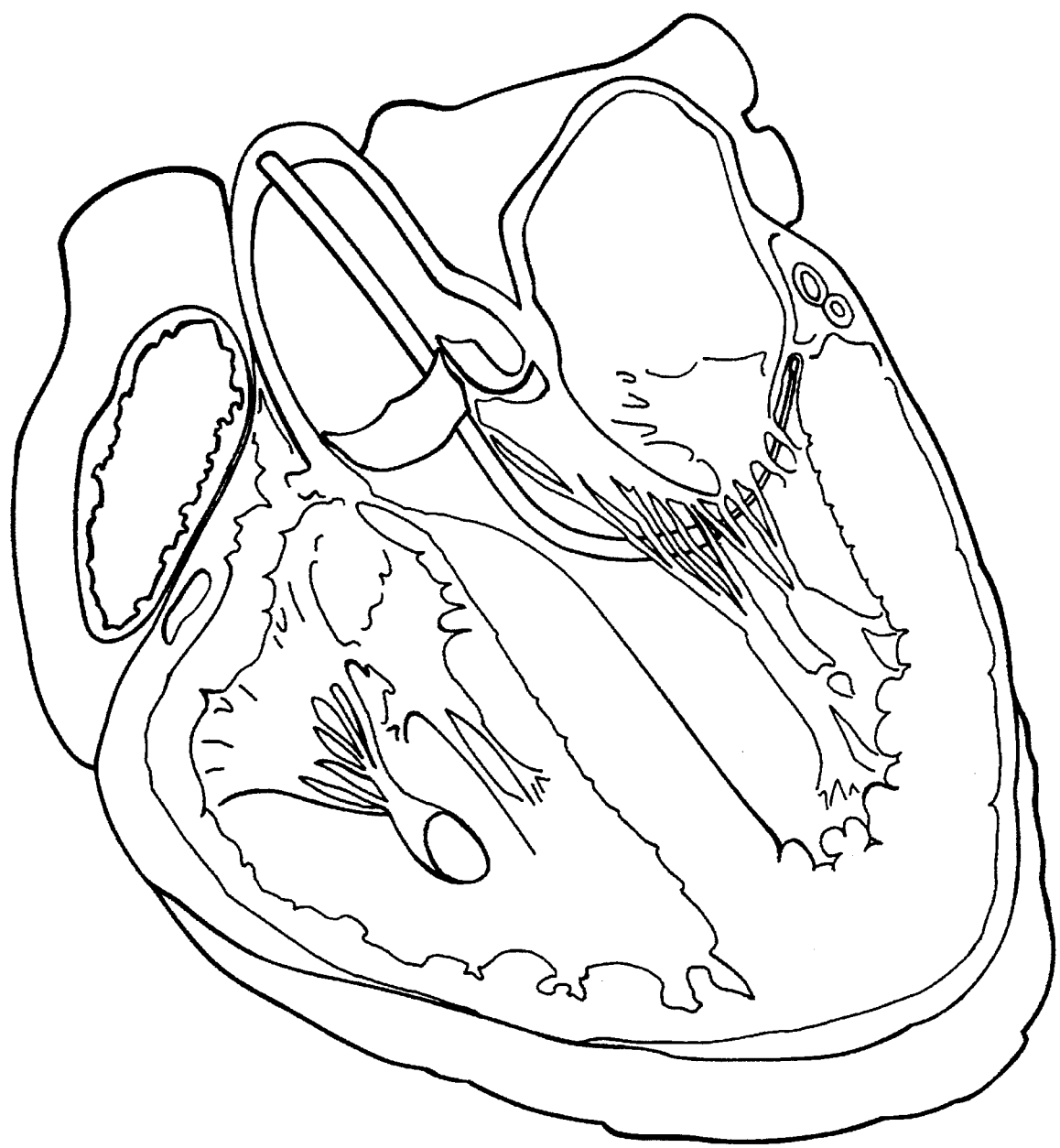
FIG. 1B is a cross-section of a portion of the left side of the heart showing one of the embodiments of guiding introducer for supporting a catheter to ablate a left lateral accessory pathway.

One end of these anomalous conduction pathways can be located either in the right atrium or in the left atrium with the other end of the pathway located in the corresponding ventricle. When the anomalous conduction pathway is located between the left atrium and the left ventricle, there are two approaches to positioning the catheter near that pathway for the appropriate medical procedure. One is to introduce the catheter into the femoral artery by a standard introducer sheath and advance it up the aorta, across the aortic valve into the left ventricle and then position its tip under the mitral valve annulus near the anomalous conduction pathway. See FIGS. 1A and 1B. This is commonly referred to as the "retrograde" approach.

The other approach, commonly referred to as the transseptal approach, is to introduce a transseptal sheath apparatus, a long single plane curve introducer, into the right femoral vein and advance it through the inferior vena cava into the right atrium. A puncture is then made through the fossa ovalis in the interatrial septum and the apparatus is advanced into the left atrium where the trocar and dilator of the apparatus are removed, leaving the sheath in position in the left atrium. The mapping or ablation catheter is then inserted through the sheath and into the left atrium and positioned on top of the mitral valve annulus near the anomalous conduction pathway. Specific positions may be chosen for the mapping or ablation on the left side of the heart, including specifically postero lateral, lateral, antero lateral, posterior, postero septal, septal, antero medial and anterior positions around the mitral valve annulus. See FIG. 1A.

Mere introduction of the ablation and mapping catheter into the left ventricle for a retrograde approach is not sufficient to effectively and efficiently perform these medical procedures, especially for the mapping or ablation of anomalous conduction pathways. The medical practitioner commonly monitors the introduction of the catheter and its progress through the vascular system by a fluoroscope. Such fluoroscopes cannot easily identify the specific features of the heart in general, and the critically important structures of the left ventricle in specific, thus making placement of the ablation electrode of the ablation catheter difficult. This placement is especially difficult as the beating heart is in motion. In addition, the ablation catheter will be moving within the left ventricle as blood is being pumped through the heart throughout the procedure. The guiding introducers of the instant invention address and solve these problems.

Referring now to FIGS. 2 through 6, the guiding introducer of the present invention for use in the left ventricle is comprised of a first, second and third section. (Each section is preferably formed as an integral portion of the entire guiding introducer without discrete sections. However, the division of the guiding introducer into three different sections better defines the shape of the guiding introducer. Each of the guiding introducers will be shown in either two or three views. In each of the views for ease of analysis, the guiding introducer will be secured to a valve for attachment to a conventional side port tubing and stop cock. In each such arrangement, the shape of the guiding introducer will be described, making reference to its position in relation to the side port and side port tubing where the proximal end of the guiding introducer is secured to the side port tubing. In the first referenced figure of each embodiment (FIGS. 2A, 3A, 4A, 5A and 6A), the side port tubing is generally viewed as if it is behind the first section of the guiding introducer. The remaining figures of each embodiment will show the guiding catheter after rotation of the guiding introducer about the axis of one of the sections. Each figure will focus upon the curved portion of the third section and the extent it is curved away from the plane formed by the first two sections when viewed from above the guiding introducer. See FIGS. 2B, 3B, 4B, 5B, and 6B.)

The first and second sections in each embodiment of the guiding introducers are generally the same shape. The first section is a conventional, generally elongated hollow, straight introducer section of sufficient length for introduction into the patient and for manipulation from the point of insertion to the specific desired location within the heart. (The overall length of the first section as shown in the drawing has been reduced for ease of viewing.)

Merged with the distal end of the first section of the guiding introducer is the second section which is curved in a smooth, generally flat curve, curving to the left as shown in FIGS. 2A, 3A, 4A, 5A and 6A. This curve has a radius of from about 1.0 in. to about 2.0 in. and preferably from about 1.3 in. to about 1.7 in. The extent of the arc of the curve is from about 160 to about 200 degrees and preferably from about 170 to about 190 degrees of arc.

The third section of the guiding introducer is merged with the distal end of the second section. The structure of the third section of the guiding introducer will depend on the location adjacent to the mitral valve being treated. As previously stated, the guiding introducers of the instant invention are used to place a mapping or ablating catheter in a position in relation to the mitral valve which is postero lateral, lateral, anterio lateral, posterior, postero septal, septal, anterio medial or anterior to the mitral valve annulus on the ventricular side of the heart. See FIG. 1A. To accomplish these procedures, the third section is generally comprised of a straight portion merged with a curved portion. The straight portion is from about 2.0 in. to about 3.5 in. in length and preferably from about 2.3 to about 3.0 in. in length. This straight portion is preferably in the same plane as are the first and second sections (within about 20 degrees of coplanar).

Figures 2A, 2B:
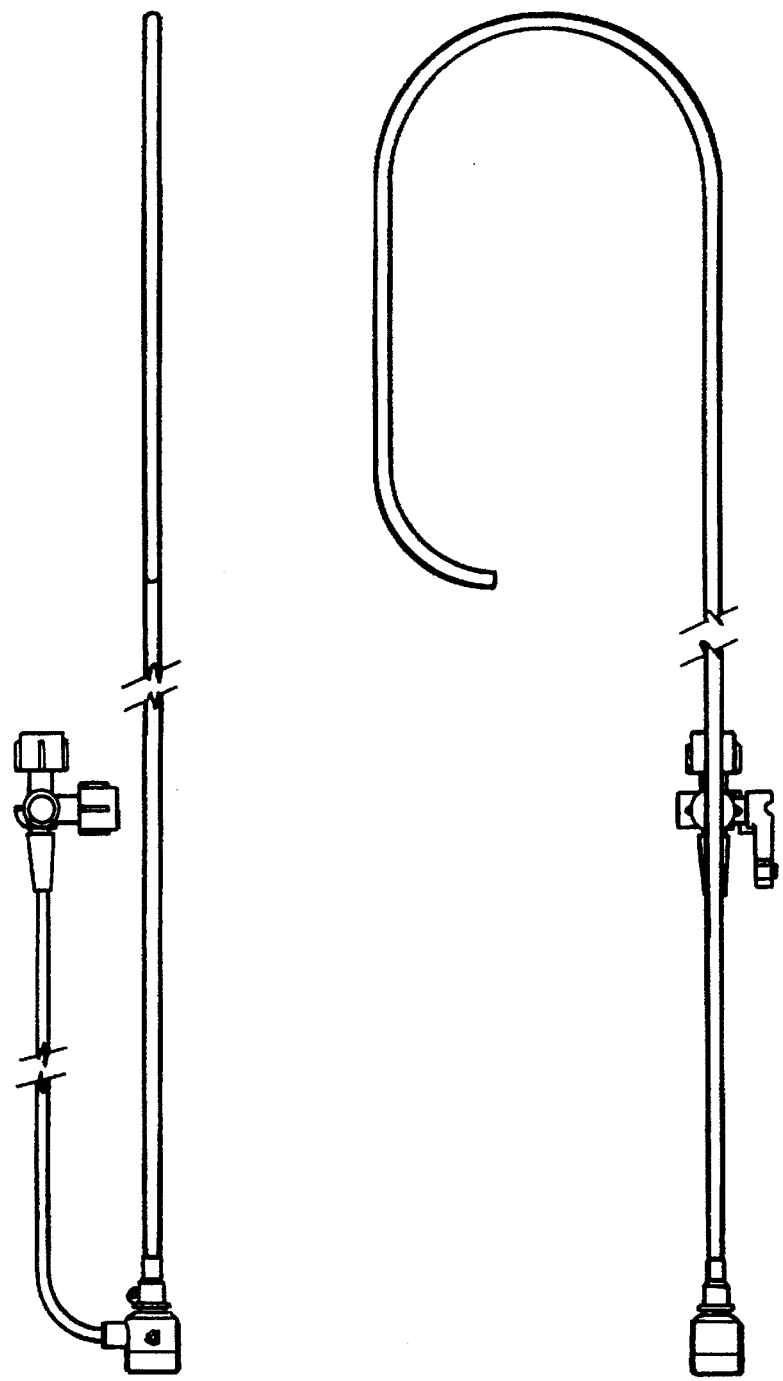
FIG. 2A is a side view of the first embodiment of the guiding introducer for use in the left ventricle around the mitral valve such that the side port tubing attached to the proximal end of the guiding introducer is located directly behind the first section of the guiding introducer.
FIG. 2B is a side view of the first embodiment of the guiding introducer rotated 90 degrees clockwise from the position of FIG. 2A, when viewed from the perspective of the proximal end of the guiding introducer, such that the side port tubing is directed to the left of the guiding introducer.

In the first embodiment (FIGS. 2A and 2B) this curved portion curves to the right (as shown in FIG. 2A) with a radius of about 0.5 to about 1.5 in. and preferably about 0.8 to about 1.2 in. This curved portion curves in an arc from about 70 to about 110 degrees and preferably from about 80 to about 100 degrees of arc. This curved portion is about 0.6 to about 1.5 in. away from the straight section and preferably about 0.8 to about 1.2 in. from the straight section ending in a distal tip. In addition to the curve toward the first section, this curved portion may also be curved out of the plane formed by the first and second sections from about 30 degrees clockwise to about 30 degrees counterclockwise when viewed from the top of the arc of the curve of the second section. This first embodiment is designed for use in the ablation and mapping of accessory pathways located lateral to the mitral valve annulus on the ventricular side. See FIG. 1B.

The distal tip of all of the guiding introducers may be, and preferably will be, tapered to form a good transition with a dilator. This tapering is preferably less than 10° and more preferably about 4° to about 7°. The guiding introducers preferably may also contain one or a multitude of radiopaque tip marker bands near the distal tip of the guiding introducer. These guiding introducers also preferably contain one or a plurality of vents near the distal tip of the guiding introducer, preferably three or four such vents. The vents are preferably located no more than about 1.00 in. from the tip of the guiding introducer and more preferably 0.10 to about 1.00 in. from the tip. The size of these vents should be in the range of about 40 to about 60/1000 of an inch in diameter. These vents are generally designed to prevent air from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the guiding introducer if no vents are provided. If such vacuum is formed, air may be forced back into the guiding introducer by the reintroduction of a catheter into the lumen of the guiding introducer. Such air embolisms could cause significant problems in the patient, including the possibility of a stroke, heart attack or other such problems common with air embolisms. The addition of vents near the distal tip of the guiding introducer prevents the formation of such vacuum by permitting fluid, presumably blood, to be drawn into the lumen of the guiding introducer as the catheter is being removed from the guiding introducer, thus preventing air from entering within the guiding introducer.

The guiding introducers may be made of any material suitable for use in humans which has a memory or permits distortion from, and substantial return to, the desired three dimensional or complex multiplanar shape. For the purpose of illustration and not limitation, the internal diameter of the guiding introducer may vary from about 6 to about 10 "French" (1 French equals ⅓ of a millimeter). Such guiding introducer can accept dilators from about 6 to about 10 French and appropriate guidewires. Obviously, if larger or smaller dilators or catheters are used in conjunction with the guiding introducers of the instant invention, modifications in size or shape can be made to the instant guiding introducers.

Variations in size and shape of the guiding introducers are also intended to encompass pediatric uses, although the preferred uses are for adult human hearts. It is well recognized that pediatric uses may require reductions in size of the various sections of the guiding introducer, in particular the first section, but without any significant modification to the shape or curves of the guiding introducer.

In addition, variations in size or shape of the guiding introducers are also intended to encompass the specialized situations that sometimes occur in patients with enlarged and rotated hearts.

Figure 3B:
FIG. 3B is a top view of the second embodiment of the guiding introducer rotated 90 degrees upward about the curved section from the position of FIG. 3A, such that the side port tubing is directed upward from the guiding introducer.
Figure 3C:
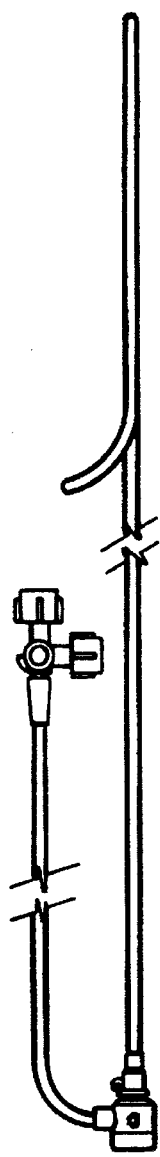
FIG. 3C is a side view of the second embodiment of the guiding introducer rotated 90 degrees clockwise from the position of FIG. 3A, when viewed from the perspective of the proximal end of the guiding introducer, such that the side port tubing is directed to the left of the guiding introducer.
Figure 3A:
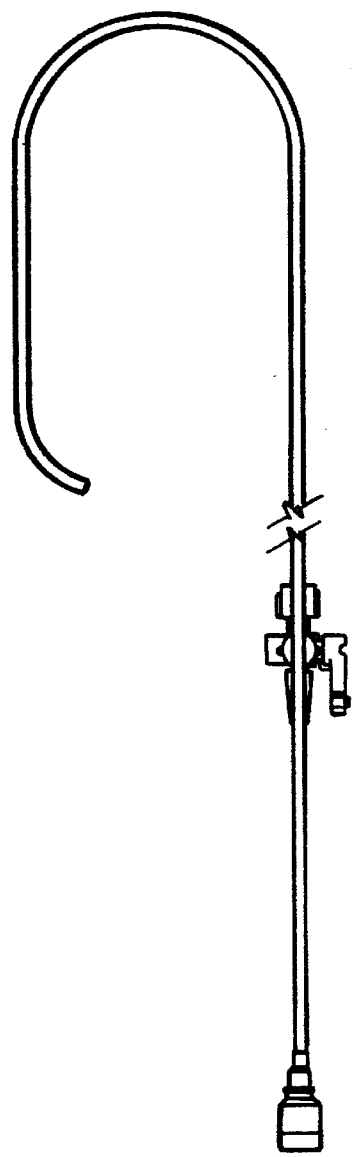
FIG. 3A is a side view of the second embodiment of the guiding introducer for use in the left ventricle, such that the side port tubing attached to the proximal end of the guiding introducer is located directly behind the first section of the guiding introducer.

The second embodiment of the guiding introducer (FIGS. 3A, 3B and 3C) is designed for use in the ablation and mapping of accessory pathways located posterior to the mitral valve annulus on the ventricular side. See FIG. 1A. In this embodiment and in the succeeding three embodiments, the first and second sections along with the straight portion of the third section are the same as was previously disclosed in the description of the first embodiment. The difference in shape lies in the curved portion of the third section. Specifically, the shape and location of the curved portion varies depending upon which accessory pathway is to be mapped and/or ablated. In the second embodiment, this curved portion curves not only toward the first section, as with the first embodiment, but also curves out of the plane of the first and second sections approximately 30 to about 60 degrees and preferably from about 40 to about 50 degrees counterclockwise when viewed from the top of the arc of the curve of the second section. (See FIG. 3B). To accomplish this out of plane curvature, the curved portion is a compound curve, curving first out of plane, as shown in FIG. 3B, and at the same time curving to the right as shown in FIG. 3A. The curve to the right of the curved portion has a radius of from about 0.7 to about 1.3 in. and preferably from about 0.9 to about 1.1 in. The arc of this curved portion is preferably from about 70 to about 110 degrees and more preferably from about 80 to about 100 degrees ending in the distal tip. See FIG. 3C. The distance from the straight portion of the third section to the distal tip of the guiding catheter is preferably from about 0.8 to about 1.2 in. and more preferably from about 0.9 to about 1.1 in. ending in the distal tip.

Figure 4B:
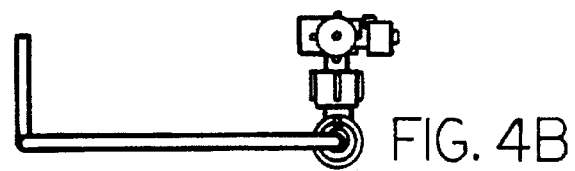
FIG. 4B is a top view of the third embodiment of the guiding introducer rotated 90 degrees upward about the curved second section from the position of FIG. 4A, such that the side port tubing is directed upward from the guiding introducer.
Figure 4C:
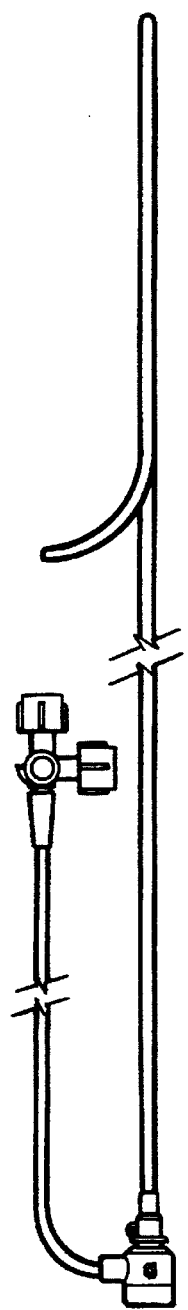
FIG. 4C is a side view of the third embodiment of the guiding introducer rotated 90 degrees clockwise from the position of FIG. 4A, when viewed from the perspective of the proximal end of the guiding introducer, such that the side port tubing is directed to the left of the guiding introducer.
Figure 4A:
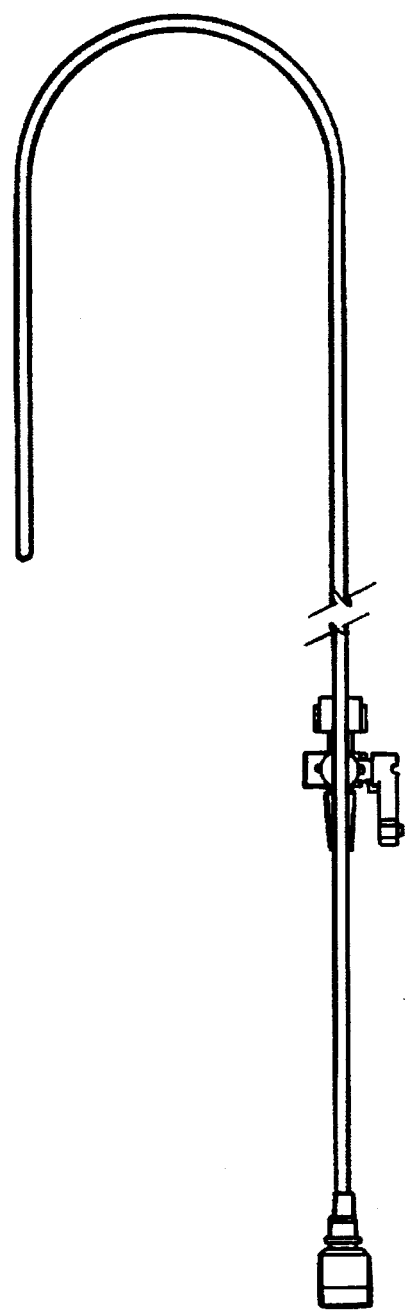
FIG. 4A is a side view of the third embodiment of the guiding introducer for use in the left ventricle, such that the side port tubing attached to the proximal end of the guiding introducer is located directly behind the first section of the guiding introducer.
Figures 5A, 5B, 5C:
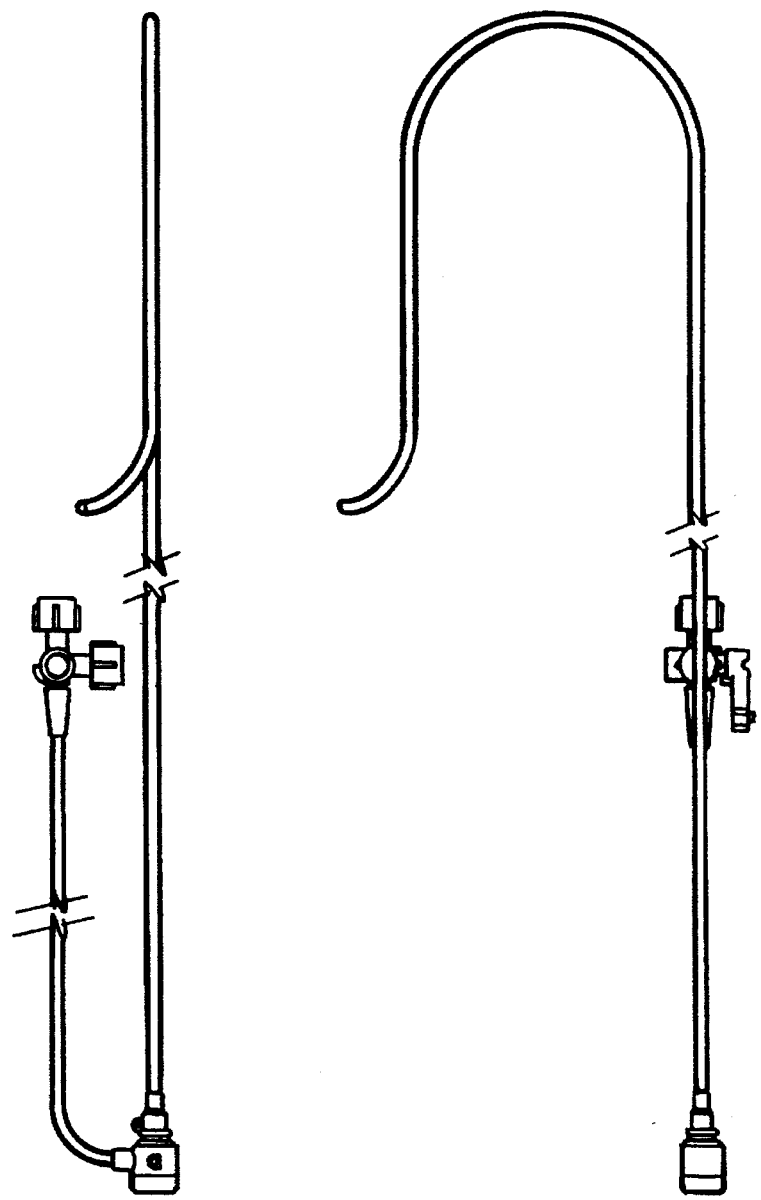
FIG. 5A is a side view of the fourth embodiment of the guiding introducer for use in the left ventricle, such that the side port tubing attached to the proximal end of the guiding introducer is located directly behind the first section of the guiding introducer.
FIG. 5B is a top view of the fourth embodiment of the guiding introducer rotated 90 degrees upward about the curved second section from the position of FIG. 5A, such that the side port tubing is directed upward from the guiding introducer.
FIG. 5C is a side view of the fourth embodiment of the guiding introducer rotated 90 degrees clockwise from the position of FIG. 5A, when viewed from the perspective of the proximal end of the guiding introducer, such that the side port tubing is directed to the left of the guiding introducer.
Figures 6A, 6B, 6C:
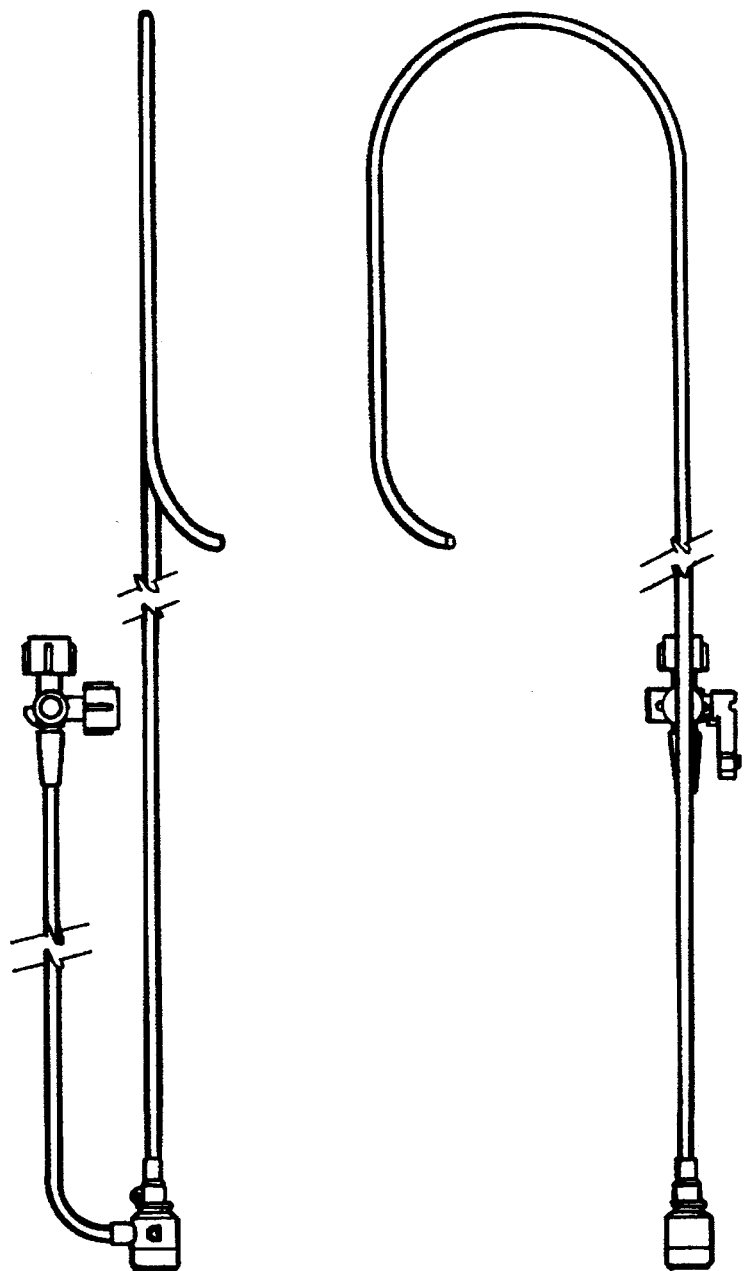
FIG. 6A is a side view of the fifth embodiment of the guiding introducer for use in the left ventricle, such that the side port tubing attached to the proximal end of the guiding introducer is located directly behind the first section of the guiding introducer.
FIG. 6B is a top view of the fifth embodiment of the guiding introducer rotated 90 degrees upward about the curved second section from the position of FIG. 6A, such that the side port tubing is directed upward from the guiding introducer.
FIG. 6C is a side view of the fifth embodiment of the guiding introducer rotated 90 degrees clockwise from the position of FIG. 6A, when viewed from the perspective of the proximal end of the guiding introducer, such that the side port tubing is directed to the left of the guiding introducer.

The third embodiment of the guiding introducer (FIGS. 4A, 4B and 4C) is designed for use in the ablation and mapping of accessory pathways located postero septal to the mitral valve annulus on the ventricular side. See FIG. 1A. The shape of this guiding catheter is similar to the second embodiment except the curved portion of the third section is rotated out of plane to a greater extent than is shown in the second embodiment. Thus, the first section, second section and straight portion of the third section of this third embodiment are generally the same as disclosed in the first and second embodiments. As with the second embodiment, the curved portion of the third section is again comprised of a compound curve, similar to the compound curve of the second embodiment except it is curved out of plane to a greater extent, from about 60 to about 115 degrees, and preferably from about 80 to about 100 degrees counterclockwise when viewed from the top of the arc of the curve of the second section. See FIG. 4B. The arc of this curved portion is preferably from about 70 to about 110 degrees and more preferably from about 80 to about 100 degrees. The curve has a radius of from about 0.7 to about 1.3 in. and preferably from about 0.9 to about 1.1 in. See FIGS. 4B and 4C. The shape and length of the curved portion is otherwise the same as was disclosed in the second embodiment. The shape of this curved portion is best shown in FIGS. 4B and 4C with FIG. 4C being the same as FIG. 4A except rotated 90 degrees to the right such that the stop cock is directed to the left of the first section of the guiding introducer. Otherwise, the lengths of the curves are the same as was disclosed in the second embodiment.

The fourth embodiment of the guiding introducer (FIGS. 5A, 5B and 5C) is designed for use in the ablation and mapping of accessory pathways located septal to the mitral valve annulus on the ventricular side. See FIG. 1A. Once again, the first, second and straight portion of the third section are the same as disclosed in the first three embodiments. The curved portion of the third section of the fourth embodiment is comprised of a compound curve, curving first out of plane and then curving to the left as shown on FIGS. 5A and 5B. The distinction between the third and fourth embodiment is the extent of the curve out of plane of this curved portion of the third section. This curved portion of the third section is out of plane of the first and second sections from about 115 to about 200 degrees and preferably from about 125 to about 160 degrees counterclockwise when viewed from the top of the arc of the curve of the second section. See FIG. 5B. The arc of this curved portion is preferably from about 70 to about 110 degrees and more preferably from about 80 to about 100 degrees. The curve has a radius of from about 0.7 to about 1.3 in. and preferably from about 0.9 to about 1.1 in. The second curve of this third section curves to the left in a manner similar to that shown in the first three embodiments with the same overall length. See FIG. 5C.

The fifth embodiment of the guiding introducer (FIGS. 6A, 6B and 6C) is designed for use in the ablation and mapping of accessory pathways located anterior to the mitral valve annulus on the ventricular side. See FIG. 1A. Once again, the first, second and the straight portion of the third section are similar to those portions in the first four embodiments. The only distinction is in the curved portion of the third section wherein this curved portion is a compound curve, curving out of plane from the first and section sections from about 200 to about 330 degrees and preferably from about 300 to about 330 degrees counterclockwise when viewed from the top of the arc of the curve of the second section. See FIG. 6B. The arc of this curved portion is preferably from about 70 to about 110 degrees and more preferably from about 80 to about 100 degrees ending in the distal tip. The curve has a radius of from about 0.7 to about 1.3 in. and preferably from about 0.9 to about 1.1 in. The second curve of this compound curve is similar to that in the first four embodiments in overall length. See FIG. 6C.

As a result of these five embodiments, five separate guiding introducers are disclosed which are similar in shape except for the curved portion of the third section. This curved portion is also similar in all five embodiments except to the extent that it is out of plane with the first and second sections.

In operation, a modified Seldinger technique is normally used for the insertion of the catheter into the femoral artery. Using this procedure, a small skin incision is made at the appropriate location to facilitate the catheter or dilator passage. The subcutaneous tissue is then dissected, followed by a puncture of the vessel with an appropriate needle with stylet positioned at a relatively shallow angle. The needle is then partially withdrawn and reinserted at a slightly different angle into the vessel, making sure that the needle remains within the vessel. A soft flexible tip of an appropriately sized guidewire is then inserted through and a short distance beyond the needle into the vessel. Firmly holding the guidewire in place, the needle is removed. The guidewire is then advanced through the artery up to the aorta, across the aortic valve into the left ventricle. With the guidewire in place, a dilator is then placed over the guidewire with the guiding introducer placed over the dilator. The dilator and guiding introducer generally form an assembly to be advanced together along the guidewire into the left ventricle. After insertion of the assembly, the guidewire and dilator are then withdrawn. The catheter to be used for analysis and/or treatment of the anomalous conduction pathways is advanced through the lumen of the guiding introducer and is placed at an appropriate location near the mitral valve annulus. The choice of the guiding introducer to be used will depend on the location of the anomalous conduction pathway, as has previously been discussed.

By choice of the desired predetermined shape of the guiding introducer in conjunction with fluoroscopic viewing, the distal portion of the guiding introducer can be manipulated to direct the ablation electrode of an ablation and/or mapping catheter placed within the lumen of the guiding introducer, to a specific internal surface with the left ventricle. In addition, by providing sufficient rigidity and support as the guiding introducer is held in place by the anatomical structure of the heart as well as the vasculature, the distal end of the guiding introducer can be maintained in that fixed location or surface position of the endocardial structure to permit the appropriate procedures to be performed. If sensing procedures are involved, the guiding introducer is placed in the desired location. At that point, the electrical activity of the heart peculiar to that location can be precisely determined by use of a sensing electrophysiology catheter placed within the guiding introducer. Further, as the guiding introducer permits precise location of catheters, an ablation catheter may be placed at a precise location for destruction by the use of energy, for example, thermal, laser, direct current (low energy DC, high energy DC or fulgutronization procedures) radiofrequency energy (possibly along with reduced temperature or iced saline or solution procedures). This precise location of the ablation catheter electrode is important as there will be no dilution of the energy delivered due to unfocused energy being dissipated over the cardiac chamber and lost in the circulating blood by a constantly moving electrode of the ablating catheter. This permits a significantly reduced amount of energy to be applied while still achieving efficient ablation. Further, time used to perform the procedure is significantly reduced over procedures where no guiding introducer is used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A process for the ablation or mapping of accessory pathways around the mitral valve of the left ventricle of a heart comprising (a) introducing into the left ventricle a guiding introducer, wherein said guiding introducer contains a lumen running lengthwise therethrough, a proximal and a distal end, and is comprised of a preselected, shaped first, second and third sections, wherein a portion of the preselected sections of the guiding introducer is held in place by the anatomy of the left ventricle, (b) introducing into the lumen of the guiding introducer an ablation or mapping catheter containing a proximal and distal end, wherein said catheter has one or more electrodes located at or near the distal end of the catheter, (c) guiding the catheter to a preselected location about the mitral valve of the heart on the ventricular side by use of the guiding introducer, and (d) mapping or ablating the preselected location about the mitral valve of the heart by use of the electrodes of the catheter.

2. The process of claim 1 wherein the first section of the guiding introducer is a generally elongated hollow straight introducer section of sufficient length for introduction into the patient and for manipulation from the point of insertion through to a desired location within the heart.

3. The process of claim 2 wherein the second section of the guiding introducer is a curved section with a radius of about 1.0 in. to about 2.0 in., and wherein the arc of the curve is from about 160 to about 200 degrees.

4. The process of claim 3 wherein the radius of the curved section of the second section is from about 1.3 in. to about 1.7 in. and wherein the arc is from about 170 to about 190 degrees.

5. The process of claim 1 wherein the third section of the guiding introducer is comprised of a straight portion and a curved portion.

6. The process of claim 5 wherein the straight portion is from about 2.0 to about 3.5 in. in length and the curved portion comprises a curve with a radius of about 0.5 to about 1.5 in., with an arc of about 70 to about 110 degrees, wherein the curve is within about 45 degrees of being in a plane formed by the first and second section, and wherein the curved portion curves generally toward the first section.

7. The process of claim 5 wherein the straight portion is from about 2.0 to about 3.5 in. in length and the curved portion comprises a curve with a radius of about 0.5 to about 1.5 in., with an arc of about 70 to about 110 degrees, wherein the curve is within about 45 to about 60 degrees of a plane formed by the first and second sections.

8. The process of claim 5 wherein the straight portion is from about 2.0 to about 3.5 in. in length and the curved portion comprises a curve with a radius of about 0.5 to about 1.5 in. with an arc of about 70 to about 110 degrees, wherein the curve is within about 60 to about 115 degrees of a plane formed by the first and second sections.

9. The process of claim 5 wherein the straight portion is from about 2.0 to about 3.5 in. in length and the curved portion comprises a curve with a radius of about 0.5 to about 1.5 in. with an arc of about 70 to about 110 degrees, wherein the curve is within about 115 to about 155 degrees of a plane formed by the first and second sections.

10. The process of claim 5 wherein the straight portion is from about 2.0 to about 3.5 in. in length and the curved portion comprises a curve with a radius of about 0.5 to about 1.5 in. with an arc of about 70 to about 110 degrees, wherein the curve is within about 155 to about 180 degrees of a plane formed by the first and second sections.

11. A process for the ablation or mapping of accessory pathways around the mitral valve of the left ventricle of a human heart using a retrograde approach comprising (a) introducing into the left ventricle a guiding introducer, wherein said guiding introducer contains a lumen running lengthwise therethrough, a proximal and a distal end, and is comprised of a preselected, shaped first, second and third sections, wherein a portion of the preselected sections of the guiding introducer is held in place by the anatomy of the left ventricle, wherein the first section is a generally elongated hollow straight section, wherein the second section contains a curved section with a radius of about 1.0 inch to about 2.0 inch, wherein the curvature of the curved section is from about 160 to about 200 degrees, wherein the third section contains a straight portion and a curved portion, wherein the straight portion is from about 2 to about 3.5 inches in length, wherein the curved portion of the third section contains a curve with a radius of about 0.5 to about 1.5 inch which is curved about 70 to about 110 degrees, wherein the curve is within about 45 degrees of being in a plane formed by the first and second sections, and wherein the curve curves generally toward the first section, (b) introducing into the lumen of the guiding introducer an ablation or mapping catheter containing a proximal and distal end, wherein said catheter has one or more electrodes located at or near the distal end of the catheter, (c) guiding the catheter to a preselected location about the mitral valve of the heart on the ventricular side by use of the guiding introducer, and (d) mapping or ablating the preselected location about the mitral valve of the heart by use of the electrodes of the catheter.

* * * * *